United States Patent
Rosengren et al.

(10) Patent No.: US 10,155,253 B2
(45) Date of Patent: Dec. 18, 2018

(54) METHOD OF ASSESSING THE CLEANNESS OF A BED SUPPORT IN A COLUMN

(71) Applicant: GE HEALTHCARE BIO-SCIENCES AB, Uppsala (SE)

(72) Inventors: Lars Rosengren, Uppsala (SE); Magnus Asplund, Uppsala (SE); Niklas Pettersson, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 91 days.

(21) Appl. No.: 15/526,537

(22) PCT Filed: Nov. 25, 2015

(86) PCT No.: PCT/EP2015/077628
§ 371 (c)(1),
(2) Date: May 12, 2017

(87) PCT Pub. No.: WO2016/083444
PCT Pub. Date: Jun. 2, 2016

(65) Prior Publication Data
US 2017/0333957 A1     Nov. 23, 2017

(30) Foreign Application Priority Data
Nov. 28, 2014   (SE) ..................... 1451452

(51) Int. Cl.
*B01D 15/22* (2006.01)
*G01N 30/60* (2006.01)
(Continued)

(52) U.S. Cl.
CPC ............ *B08B 9/0321* (2013.01); *B01D 15/22* (2013.01); *G01L 13/00* (2013.01); *G01N 30/603* (2013.01); *G01N 30/6052* (2013.01)

(58) Field of Classification Search
CPC ........ B01D 15/00; B01D 15/22; B08B 9/032; B08B 9/0321; G01L 13/00; G01L 15/00;
(Continued)

(56) References Cited

U.S. PATENT DOCUMENTS 5,338,448 A * 8/1994 Gjerde ................. B01D 15/08
                                                                    210/198.2
6,190,560 B1   2/2001 Mann
(Continued)

FOREIGN PATENT DOCUMENTS

WO       94/08685 A1    4/1994

OTHER PUBLICATIONS

PCT International Search Report and Written Opinion for PCT Application No. PCT/EP2015/077628 dated Feb. 11, 2016 (13 pages).

*Primary Examiner* — Nguyen Q. Ha
(74) *Attorney, Agent, or Firm* — Eversheds Sutherland (US) LLP

(57) ABSTRACT

The invention discloses a method for individually assessing the cleanness of at least one of an upper (2) and a lower (3) bed support in a process column (1). The method comprises the steps of: a) providing a process column (1) comprising an upper (2) and a lower (3) bed support, a column chamber, a movable adaptor (5), an upper outlet (6) and a lower outlet (7); b) conveying liquid through one of the lower (3) and upper (2) bed supports, e.g. by moving the adaptor (5) downwards at a predetermined rate with one of the upper and lower outlets closed and the other open to force liquid through one of the lower and upper bed supports, and; c) measuring the differential pressure over the bed support through which liquid passes.

20 Claims, 5 Drawing Sheets

(51) Int. Cl.
  *B08B 9/032* (2006.01)
  *G01L 13/00* (2006.01)
(58) Field of Classification Search
  CPC ........ G01L 15/08; G01N 30/02; G01N 30/60;
  G01N 30/603; G01N 30/6052
  See application file for complete search history.

(56) References Cited

U.S. PATENT DOCUMENTS

| | | |
|---|---|---|
| 6,736,974 B1 | 5/2004 | Mann |
| 2009/0039008 A1 | 2/2009 | Davis et al. |
| 2013/0248430 A1 | 9/2013 | Gu |
| 2014/0021116 A1* | 1/2014 | Ford ........................ H05B 6/10 |
| | | 210/198.2 |

\* cited by examiner

METHOD OF ASSESSING THE CLEANNESS OF A BED SUPPORT IN A COLUMN

CROSS REFERENCE TO RELATED APPLICATIONS

This application claims the priority benefit of PCT/EP2015/077628 filed on Nov. 25, 2015 which claims priority benefit of Swedish Application No. 1451452-5filed Nov. 28, 2014. The entire contents of which are hereby incorporated by reference herein.

TECHNICAL FIELD OF THE INVENTION

The present invention relates to process columns, and more particularly to a method of measuring the cleanness of bed supports in a process column. It also relates to a computer program for automation of the method.

BACKGROUND OF THE INVENTION

Axial columns with packed beds of particles are commonly used both in process scale chromatography and in solid-phase synthesis of e.g. peptides or oligonucleotides. In chromatography, the bed contains adsorbent particles for selectively binding and certain feed components and in solid phase synthesis the particles used have suitable reactive groups for stepwise synthesis of the peptide or oligonucleotide. In such columns, the packed particle bed is usually stabilized by compression in an axial direction, sometimes using a movable adaptor (which can alternatively be called a piston). Traditionally the adaptor has been movable by means of threaded rods or hydraulics, but more recently columns with adaptor movement controlled by step motors have also become available.

The particle bed is confined between two bed supports, which typically comprise porous plates or meshes facing the bed. The bed supports have pores with diameter significantly smaller than the average diameter of the particles in the bed. Liquid is conveyed via a coarse channel distributor through the bed support into the bed and on the outlet side the liquid passes through the other bed support via a distributor into the outlet. The bed supports can during use be contaminated both by small bed particles (fines) entering into the pores of the supports (plugging) and by fouling, i.e. deposition of particulate or precipitated material originating from the liquid passed through the column. Such contamination will lead to increased back pressures and may also cause inhomogeneities in the flow distribution of the column which will affect the performance negatively.

In e.g. the biopharmaceutical industry it is common practice to use the packed bed in a chromatography column for a large number of separation cycles. When the lifetime of the packed bed has been reached, the column is unpacked and repacked with a new bed. In older types of chromatography columns the unpacking and repacking necessitated disassembly of the column and it was then easy to inspect the bed supports and replace or clean them if needed. Modern chromatography columns can however be unpacked and repacked without disassembly through the use of packing/unpacking nozzles, as described in e.g. WO96/10451, WO99/22234, WO2008/134413 and U.S. Pat. No. 6,190,560. Disassembly of the column only in order to inspect and/or exchange the bed supports is cumbersome and costly and also involves a risk of accidental contamination of the flowpaths and there is therefore a need for a method to assess the cleanness of each bed support without disassembling the column.

SUMMARY OF THE INVENTION

One aspect of the invention is to provide a method for individually assessing the cleanness of at least one bed support in a process column. This is achieved with a method as defined in claim 1.

One advantage is that the supports can be assessed individually without disassembly of the column. A further advantage is that the method is easy to perform using equipment already available with the column.

A second aspect of the invention is to provide a computer program for assessing the cleanness of at least one bed support in a process column.

Further suitable embodiments of the invention are described in the dependent claims.

DEFINITIONS

It should be understood by those skilled in the art that the use of directional terms such as above, below, upper, lower, upward, downward, top, bottom and the like are used in relation to the illustrative embodiments as they are depicted in the figures, the upward direction being toward the top of the corresponding figure and the downward direction being toward the bottom of the corresponding figure.

The use of the terms "inlet" and "outlet" does not exclude the possibility of reverse flow direction, i.e. that a flow enters the column via the outlet and exits via the inlet.

DRAWINGS

DETAILED DESCRIPTION OF EMBODIMENTS

Figure 1:
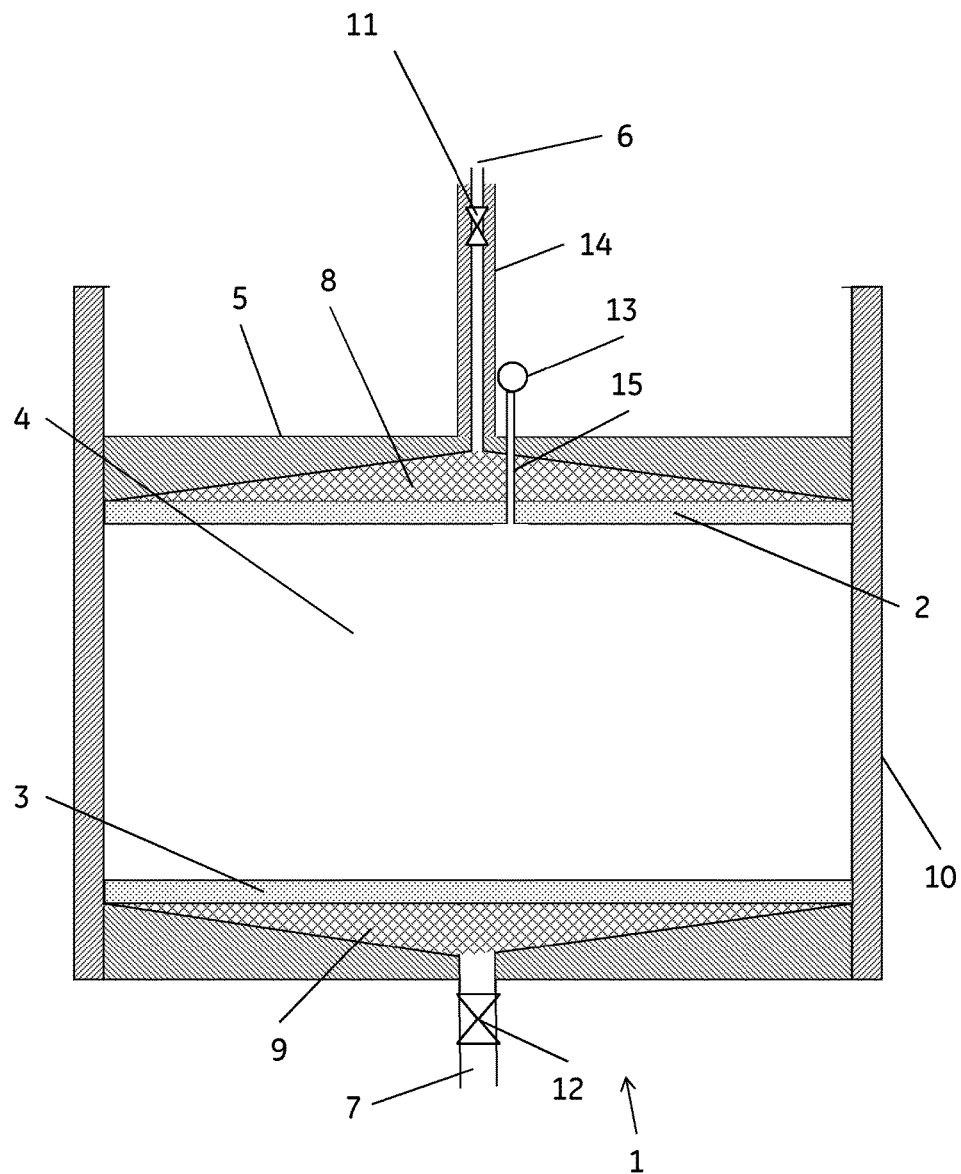
FIG. 1 shows a column for use with the method of the invention.
Figure 2:
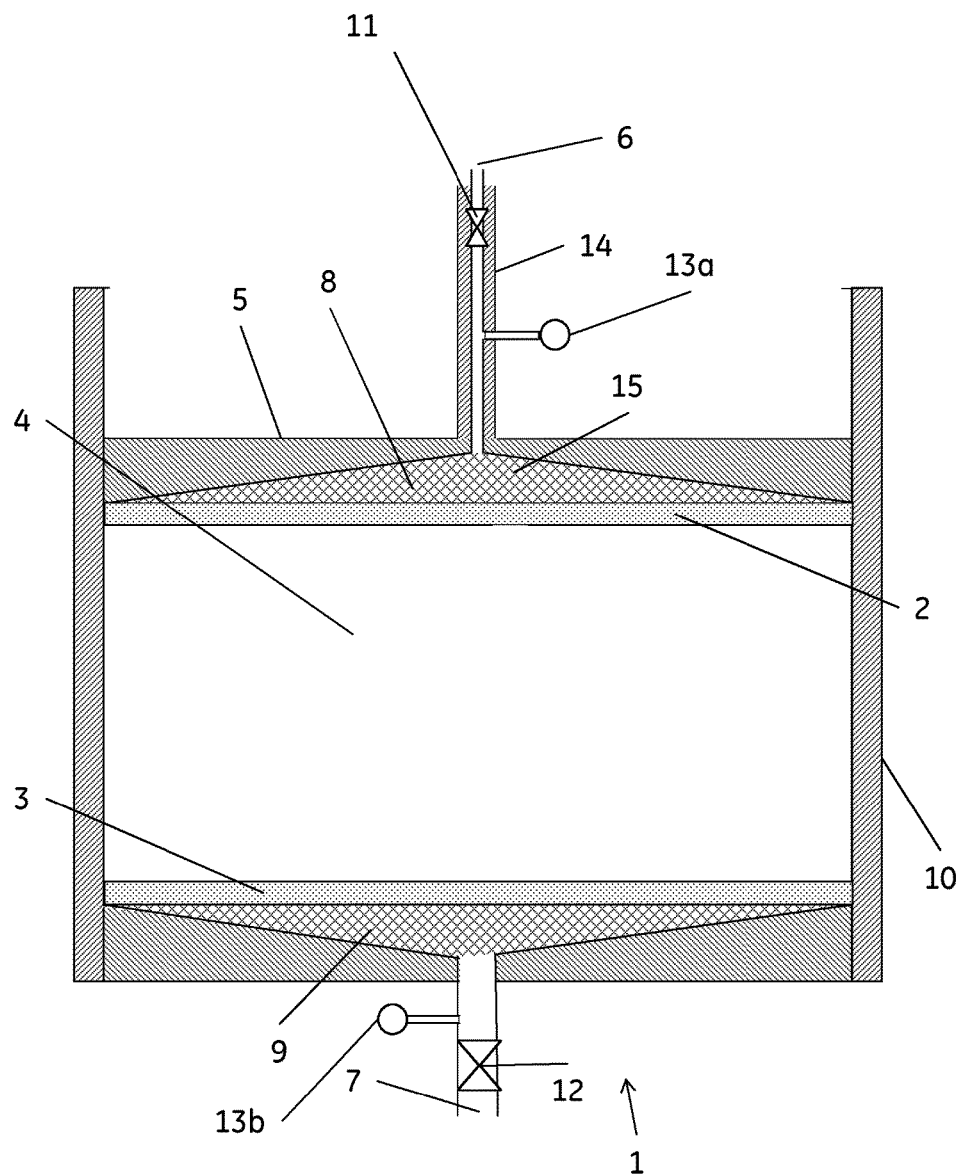
FIG. 2 shows the column of FIG. 1 with an alternative pressure gauge arrangement.
Figure 3:
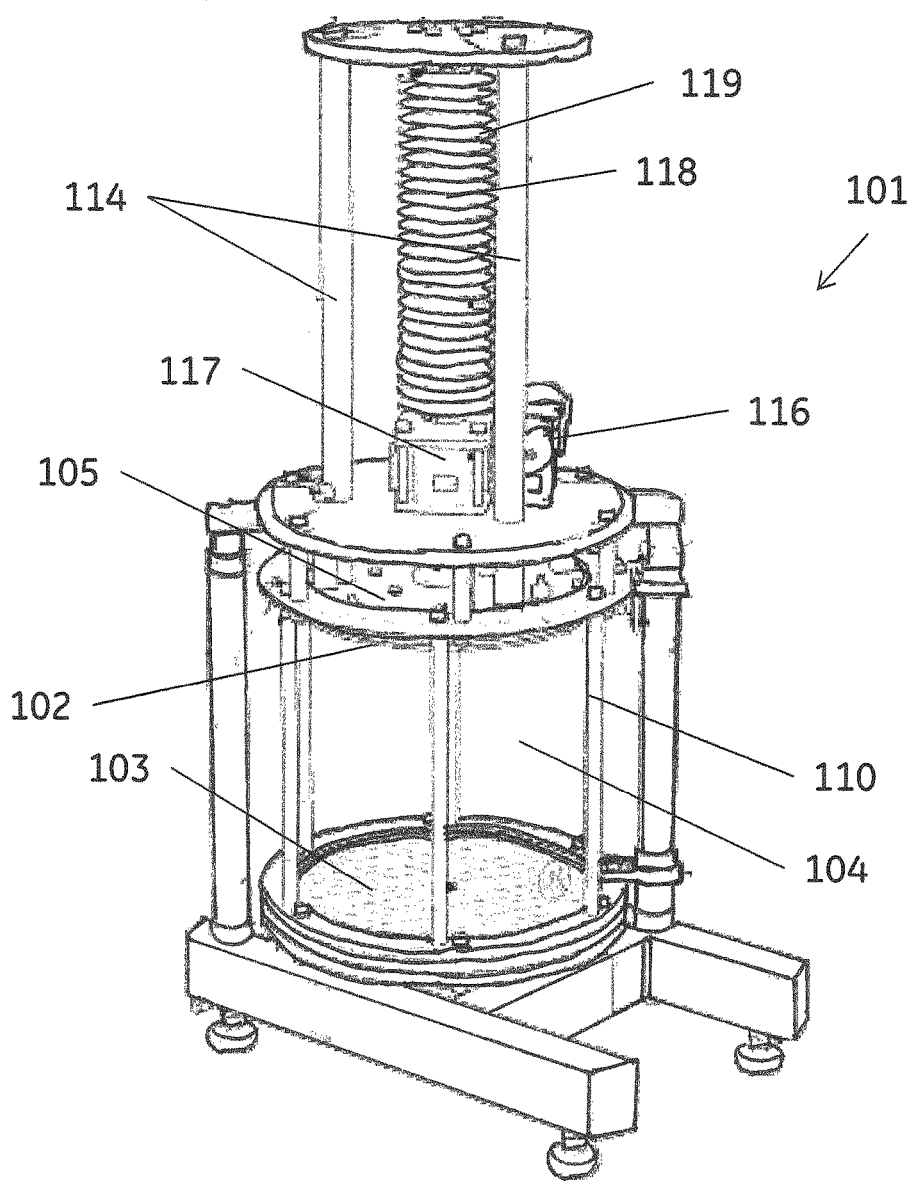
FIG. 3 shows another example of a column for use with the method of the invention.
Figure 4:
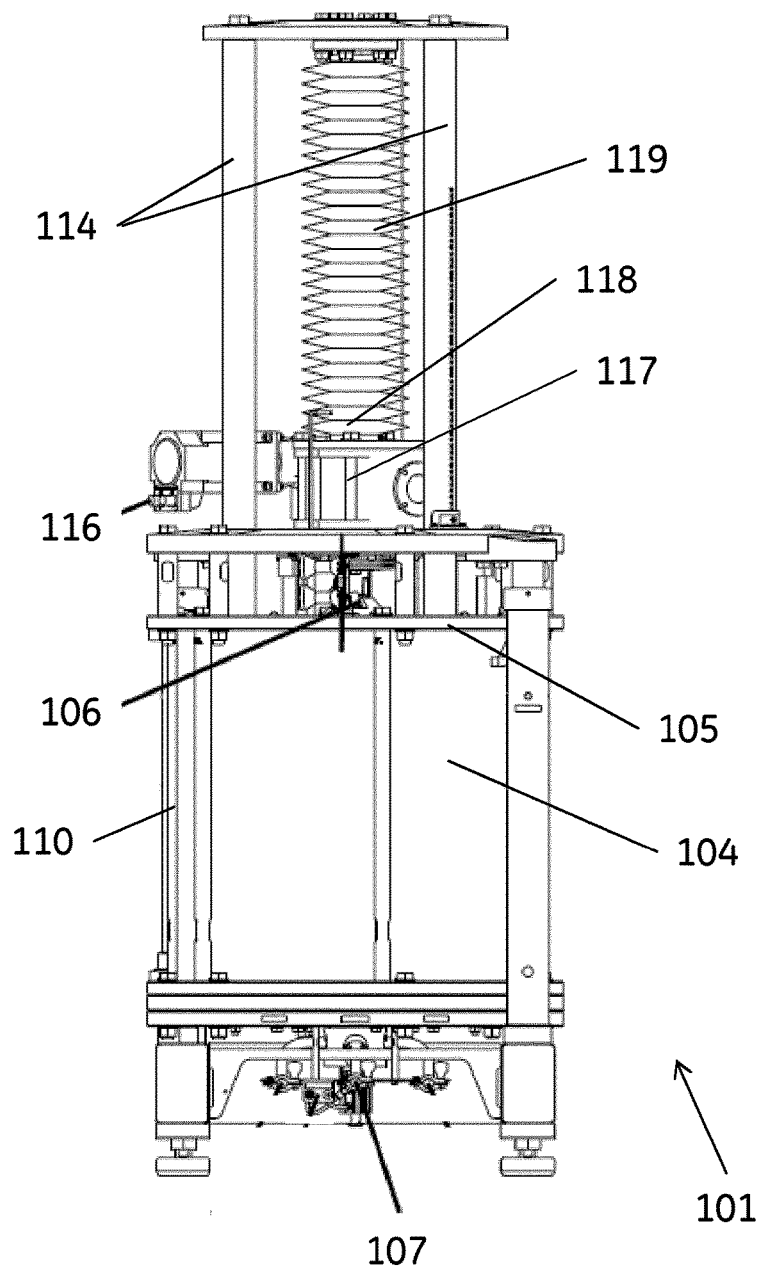
FIG. 4 shows a side view of the column of FIG. 2.
Figure 5:
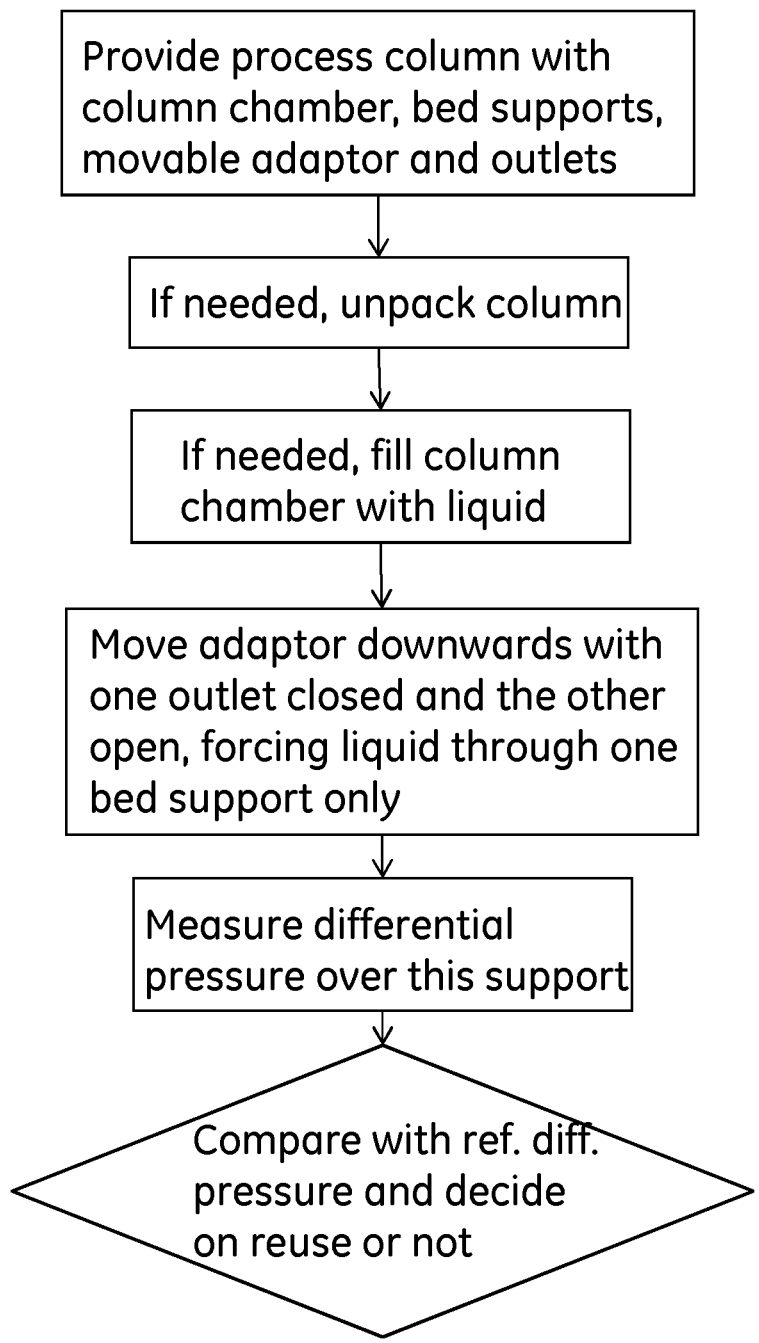
FIG. 5 shows a flow diagram of an embodiment of the method.

In one aspect, illustrated by FIGS. 1-5, the present invention discloses a method for individually assessing the cleanness of at least one, such as both, of an upper 2; 102 and a lower 3; 103 bed support in a process column 1; 101, such as a chromatography column or a solid phase synthesis column. The method comprises the steps of:

a) Providing a process column 1; 101 in an assembled state, comprising an upper 2; 102 and a lower 3; 103 liquid-permeable bed support, a generally cylindrical column chamber 4; 104 arranged to contain a packed bed, an upper outlet 6; 106 and a lower outlet 7; 107. The column can also comprise an upper 8 and a lower 9 distributor between the respective bed support 2; 102,3; 103 and outlet 6; 106,7; 107, a column wall 10; 110, an upper 11 and a lower 12 closure valve adapted to close the respective outlet 6; 106,7; 107 and at least one pressure gauge 13; 13a,13b, adapted to measure the pressure in the column chamber, e.g. by being in directly fluidic connection with the chamber by a pressure gauge tube 15. The column can further comprise an adaptor 5; 105, which may be movable and in slidable sealing abutment with the column wall, such that liquid is forced out from the column chamber through either the upper or the lower outlet if the adaptor is moved downwards. The adaptor can contain the upper distributor, with the upper bed support releasably attached to the adaptor. One or more piston rods 14; 114 may also be attached to the adaptor. The column can be an axial column and the column chamber may be delimited by the column wall and the upper and lower bed supports. The distributors can be structures known in the art of process columns and suitable for distribution of flowing liquid from a tube over the surface of a bed support. Suitably, the column may be provided without any packed bed in the column chamber and the chamber may be filled with a liquid (e.g. water), suitably such that the column chamber is essentially free from air pockets. If needed, this may be achieved by unpacking the column and/or by filling the column chamber with a liquid before step b).

b) Conveying liquid through one of the lower and upper bed supports. This can e.g. be achieved by moving a movable adaptor downwards, with one of the upper and lower outlets being closed and the other open, such that liquid is forced through only one of the lower and upper bed supports. To close the upper outlet, the upper closure valve may be used and to close the lower outlet, the lower closure valve may be used. With the lower outlet closed, the liquid will be forced through the upper bed support and with the upper outlet closed, the liquid will be forced through the lower bed support.

c) Measuring the differential pressure $\Delta P$ over the bed support that the liquid is forced through. Pressure gauge 13 of FIG. 1 (directly connected to the chamber) can be used for the measurement, e.g. by measuring the static pressure inside the chamber while no liquid is conveyed through a bed support, such as when the adaptor is not moving, and subtracting this reading from the pressure reading when the adaptor is moving. The pressure downstream of the bed support can usually be considered equal to the ambient atmospheric pressure. The substractive method provides accurate determination of the pressure drop with a single pressure gauge. Alternatively, a plurality of pressure gauges may be used, allowing pressure measurement on both sides of the bed support. If the liquid is conveyed by movement of the adaptor 5, it is also possible to use a pressure gauge setup as in FIG. 2, where pressure gauge 13*a* can be used to measure the pressure when valve 11 is closed and liquid is forced only through lower bed support 3 and, vice versa, pressure gauge 13*b* can be used when valve 12 is closed and liquid is forced only through upper bed support 2. Any pressure drop over the distributors can be disregarded, as the distributors have significantly wider channels than the bed supports and the bed supports are much more prone to plugging and fouling.

In certain embodiments the adaptor is moved downwards at a predetermined velocity v. This will generate a volumetric liquid flow rate F=v*A, where A is the internal cross-section area of the column chamber, i.e. $r^2 * \pi$, where r is the internal radius of the chamber. v may also be varied and $\Delta P$ measured for each individual value of v or F. Alternatively, the adaptor is moved downwards at a velocity v that produces a predetermined differential pressure $\Delta P$, which may be controlled e.g. by a feedback loop.

In some embodiments, the method further comprises a step d) of comparing the differential pressure $\Delta P$ with a reference differential pressure $\Delta P_{ref}$ and deciding whether the bed support in question can be reused. The reference differential pressure can e.g. be a differential pressure over a clean or unused bed support, which is determined under identical or substantially identical conditions as the measurement in step c). With substantially identical conditions can e.g. be meant that the measurement is made in the same type of column setup (e.g. in the same column) with the same type of liquid, with the flow rate deviating less than 10%, such as less than 5% or less than 2%, and at a temperature deviating less than 5° C., such as less than 2° C. or less than 1° C., to avoid liquid viscosity variations. $\Delta P_{ref}$ can e.g. be measured initially when a clean support has been mounted in the column The decision criterion may e.g. be that the bed support is reused if $\Delta P/\Delta P_{ref}$ is less than 2, such as less than 1.5, less than 1.2 or less than 1.1.

In some embodiments, the method further comprises repeating steps b), c) and optionally d) for the other bed support. If the bed support assessed in steps b) and c) has been the upper bed support, this can involve closing the upper outlet and opening the lower outlet and then repeating the steps. Vice versa, if the lower bed support has been assessed, the lower outlet is closed and the upper outlet opened and the steps repeated.

In certain embodiments, the adaptor 5; 105 is moved with a motor, such as a step motor or other type of high precision motor. A step motor 116, e.g. arranged to move the adaptor via one or more piston rods 14; 114 and optionally a gear 117, e.g. a worm gear, and a driving rod 118, e.g. a threaded rod, which may be covered by a bellows 119, is capable of providing a smooth movement of the adaptor with high precision in the velocity and the momentaneous position of the adaptor. This provides for accurate and reproducible flow rate and differential pressure readings and avoids any pulsations which may disturb the measurement. Alternatively, the adaptor may be moved e.g. by a hydraulic system.

In some embodiments, e.g. for columns which do not have a movable adaptor or where the adaptor cannot be moved with high precision, the conveying of liquid through one of the lower and upper bed supports in step b) can be achieved by the use of an external pump. Advantageously the pump is able to deliver a precise flow rate without pulsations. In these embodiments, the pressure gauge setup of FIG. 1 is suitable, with the liquid conveyed into either the upper outlet 6 (when assessing the lower bed support) or the lower outlet 7 (when assessing the upper bed support), with both valves 11 and 12 open, and with the pressure measured by pressure gauge 13 both during conveying of the liquid and at standstill. The difference between the readings is then taken as the differential pressure $\Delta P$ over the assessed bed support.

In some embodiments, the method further comprises a step e) of conveying a cleaning liquid through at least one of the upper and lower bed supports. This step may e.g. be performed before step b) or before step a"), in which case the assessment is made on the bed supports after an attempt to clean them in place in order to see if the cleaning was sufficient or if the supports need to be replaced or cleaned offline. Step e) may also be performed after step c) or d) depending on the outcome of these steps. In this case it can also be advantageous to repeat steps b), c) and optionally d) to assess the efficiency of the cleaning.

In certain embodiments, steps b), c) and optionally d) are controlled by a control unit. The control unit can be e.g. a computer or a programmable logic controller (PLC). This provides for automation of the procedure and can be achieved by electrical or electromagnetical connections between the control unit and the closure valves, the pressure gauge (which may be a pressure sensor providing an electric or electromagnetic signal) and any means for moving the adaptor, such as e.g. the step motor discussed above, a hydraulic pump or a motor driving a threaded rod.

The control unit may also control any feedback loop as discussed above. If step d) is also controlled by the control unit, an automated decision-making process may be implemented, including storage and/or print-out of documentation of the decision. Also steps a') and a") may be controlled by the control unit, if desired, to obtain a completely automatic procedure.

In some embodiments, the column chamber has an inner diameter of at least 10 cm, such as at least 30 cm or at least 100 cm. The method is particularly useful for large columns where column disassembly is a very cumbersome process.

In certain embodiments, at least one, such as both, of said upper and lower bed supports is/are porous with an average (volume-weighted, circle equivalent) pore diameter of 5-250 micrometers, such as 10-100, 5-100, 5-60 or 5-20 micrometers. With small pore sizes, the effect of contamination on the back pressure of the bed supports will be higher, increasing the sensitivity of the test and also the need to perform the test. The bed supports have an open pore structure to allow for liquid passage and may e.g. comprise woven meshes, nonwoven fibrous structures or sintered powder-type porous materials. The materials used in the bed supports can be e.g. metals, plastics, ceramics or glass. For larger columns, metals and plastics have the advantage of not being brittle.

In some embodiments, at least one of said upper and lower bed supports comprises a metal mesh, such as a sintered multilayer metal mesh. Commercially available sintered multilayer metal meshes (e.g. stainless steel meshes) are robust and provide suitable pore structures.

In certain embodiments, at least one of said upper and lower bed supports comprises a porous plastic, such as a sintered porous plastic. Commercially available sintered porous plastics, e.g. polyolefins such as polypropylene or polyethylene, provide high corrosion resistance combined with suitable pore structures.

In a second aspect, the invention discloses a computer program on a readable medium. This program comprises instructions for causing a control unit, e.g. a computer or a PLC, to perform at least steps b) and c), and optionally also step d) as described above. Alternatively, the program can provide instructions for manual operation of these steps.

EXAMPLES

An Axichrom 1600 column (GE Healthcare) with 10 micrometer pore size stainless steel multilayer mesh bed supports of 160 cm diameter was repacked and run several times with crosslinked agarose beads. Before the first packing (after ultrasonic cleaning of the supports) as well as before the third packing and before the fifth packing, the following assessment procedure was performed.

The column was primed with room-temperature water and the adaptor was moved downwards at constant velocity of 600 cm/h. First, the bottom valves were closed, such that the water was forced through the upper bed support to the upper outlet, and the pressure in the column chamber was measured with a pressure gauge at the bottom mobile phase inlet. Then the bottom mobile phase outlet valve was opened and all top valves closed, to force the water through the lower bed support to the lower outlet, and the column chamber pressure was measured with a pressure gauge at the top mobile phase inlet. The pressure readings are shown in Table 1.

TABLE 1

| | Pressure upper bed support | Pressure lower bed support |
| --- | --- | --- |
| Before use (after ultrasonic cleaning) | 0.10 bar | 0.20 bar |
| Before third packing | 0.10 bar | 0.21 bar |
| Before fifth packing | 0.10 bar | 0.25 bar |

The data show that the upper bed support was not affected by the repeated packings and runs, while some plugging of the lower bed support had occurred.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Any patents or patent applications mentioned in the text are hereby incorporated by reference in their entireties, as if individually incorporated.

The invention claimed is:

1. A method for individually assessing cleanness of one of an upper and a lower bed support in a process column, said method comprising steps of:
   a) providing a process column comprising an upper and a lower bed support, a column chamber, an upper outlet and a lower outlet;
   b) conveying liquid through one of the upper and the lower bed support, and
   c) measuring a differential pressure over said one of the upper and the lower bed support.

2. The method of claim 1, wherein said column further comprises a movable adaptor and wherein in step b) one of said upper and lower outlets is closed and the other is open and liquid is conveyed through said one of the lower and upper bed supports by moving said adaptor downwards.

3. The method of claim 2, wherein said adaptor is moved with a step motor (116).

4. The method of claim 2, wherein the adaptor is moved with a predetermined velocity.

5. The method of claim 2, wherein the adaptor is moved with a velocity that produces a predetermined differential pressure.

6. The method of claim 2, wherein said upper bed support is attached to said movable adaptor.

7. The method of claim 1, further comprising an optional step a'), before step b), of optionally unpacking said process column.

8. The method of claim 1, further comprising an optional step a"), before step b), of filling said column chamber with a liquid.

9. The method of claim 1, further comprising a step d) of comparing said differential pressure with a reference differential pressure and deciding whether said one of the lower and upper bed supports can be reused.

10. The method of claim 9, wherein said reference differential pressure is a differential pressure over a clean bed support, determined under substantially identical conditions.

11. The method of claim 9, further comprising repeating steps b), c) and optionally d) for the other of said lower and upper bed supports.

12. The method of claim 9, further comprising a step e) of conveying a cleaning liquid through at least one of said upper and lower bed supports.

13. The method of claim 9, wherein steps b), c) and optionally d) are controlled by a control unit.

14. A computer program on a readable medium, comprising instructions for causing a control unit, such as a computer, to perform steps b), c) and optionally d) of the method of claim 9.

15. The method of claim 1, wherein said process column is a chromatography column.

16. The method of claim 1, wherein said column chamber has an inner diameter of at least 10 cm, such as at least 30 cm or at least 100 cm.

17. The method of claim 1 wherein at least one of said upper and lower bed supports is porous with an average pore diameter of 5-250 micrometers, such as 5-60 micrometers.

18. The method of claim 1 wherein at least one of said upper and lower bed supports comprises a metal mesh, such as a multilayer metal mesh.

19. The method of claim 1 wherein at least one of said upper and lower bed supports comprises a porous plastic, such as a sintered porous plastic.

20. The method of claim 1, wherein said column comprises at least one pressure gauge, adapted to measure a pressure in said column chamber.

\* \* \* \* \*